United States Patent
Schwieger et al.

(10) Patent No.: US 9,510,860 B2
(45) Date of Patent: Dec. 6, 2016

(54) SLEEVE FOR A TRANSFIXATION DEVICE FOR AN EXTERNAL SKELETAL FIXATOR

(75) Inventors: Karsten Schwieger, Davos (CH); Victor Sprenger, Milton (CA)

(73) Assignee: AO Technology AG, Chur (CH)

( * ) Notice: Subject to any disclaimer, the term of this patent is extended or adjusted under 35 U.S.C. 154(b) by 964 days.

(21) Appl. No.: 12/598,142

(22) PCT Filed: Apr. 30, 2007

(86) PCT No.: PCT/CH2007/000210
§ 371 (c)(1),
(2), (4) Date: Jan. 8, 2010

(87) PCT Pub. No.: WO2008/131568
PCT Pub. Date: Nov. 6, 2008

(65) Prior Publication Data
US 2010/0125273 A1    May 20, 2010

(51) Int. Cl.
*A61F 5/04* (2006.01)
*A61B 17/68* (2006.01)
*A61B 17/62* (2006.01)
*A61B 17/88* (2006.01)
*A61D 1/00* (2006.01)

(52) U.S. Cl.
CPC ............ *A61B 17/683* (2013.01); *A61B 17/62* (2013.01); *A61B 17/686* (2013.01); *A61B 17/8869* (2013.01); *A61D 1/00* (2013.01)

(58) Field of Classification Search
CPC ..... A61B 17/62; A61B 17/683; A61B 17/686; A61B 17/64; A61B 17/6408; A61B 17/6416; A61B 17/6425; A61B 17/6433; A61B 17/6441; A61B 17/645; A61B 17/6458; A61B 17/6466; A61B 17/6475; A61B 17/6483; A61B 17/6491
USPC ............... 606/54–59, 60, 62–64, 87–90, 66, 302,606/303, 304, 309, 310, 323, 326, 329
See application file for complete search history.

(56) References Cited

U.S. PATENT DOCUMENTS

| | | | | |
|---|---|---|---|---|
| 1,752,752 A | * | 4/1930 | Ogden | ............................ 411/68 |
| 4,397,307 A | * | 8/1983 | Keller | ................ A61B 17/6408 606/130 |
| 4,590,930 A | * | 5/1986 | Kurth et al. | .................... 606/63 |

(Continued)

FOREIGN PATENT DOCUMENTS

| | | |
|---|---|---|
| DE | 19611881 C1 | 6/1997 |
| EP | 0384001 A1 | 8/1990 |
| EP | 0786235 A2 | 7/1997 |

*Primary Examiner* — Jan Christopher Merene
*Assistant Examiner* — Atiya Mahmud
(74) *Attorney, Agent, or Firm* — Rankin, Hill & Clark LLP

(57) ABSTRACT

Disclosed is a sleeve for a transfixation device for an external skeletal fixator having a longitudinal axis, a right portion, a left portion, an outer wall, an interior wall and a lumen. The sleeve is implantable across the opposed cortices of a long bone. The lumen is adapted to receive a pin that is connectable to an external supporting structure of the external skeletal fixator. The lumen includes at least one contraction in the right portion and at least one contraction in the left portion. The at least two contractions serve as supports for the pin for avoiding contact between the pin and the interior wall, except at the contractions. Also disclosed is a transfixation device for an external skeletal fixator including a sleeve such as described and one or more pins.

21 Claims, 4 Drawing Sheets

(56) References Cited

U.S. PATENT DOCUMENTS

| | | | |
|---|---|---|---|
| 4,923,458 A * | 5/1990 | Fischer | 606/59 |
| 5,087,258 A * | 2/1992 | Schewior | 606/56 |
| 5,578,041 A * | 11/1996 | Nash et al. | 606/54 |
| 5,919,194 A * | 7/1999 | Anderson | 606/313 |
| 6,200,317 B1 * | 3/2001 | Aalsma et al. | 606/62 |
| 6,277,136 B1 * | 8/2001 | Bonutti | 606/190 |
| 6,537,274 B1 * | 3/2003 | Katz | 606/56 |
| 6,706,042 B2 * | 3/2004 | Taylor | A61B 17/66 606/57 |
| 7,837,731 B2 * | 11/2010 | Sklar | 623/13.14 |
| 8,109,975 B2 * | 2/2012 | Veldman et al. | 606/257 |
| 2003/0036761 A1 * | 2/2003 | Smothers | A61B 17/60 424/426 |
| 2003/0073999 A1 * | 4/2003 | Putnam | 606/62 |
| 2005/0038437 A1 * | 2/2005 | McDevitt et al. | 606/72 |
| 2005/0216006 A1 * | 9/2005 | Orbay et al. | 606/62 |
| 2006/0155275 A1 * | 7/2006 | Dongar et al. | 606/59 |
| 2008/0108995 A1 * | 5/2008 | Conway et al. | 606/63 |

\* cited by examiner

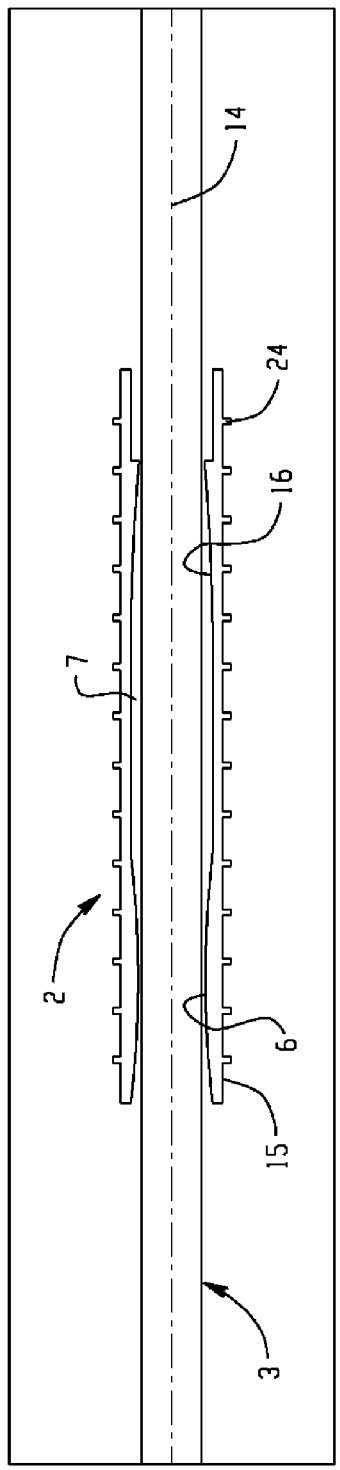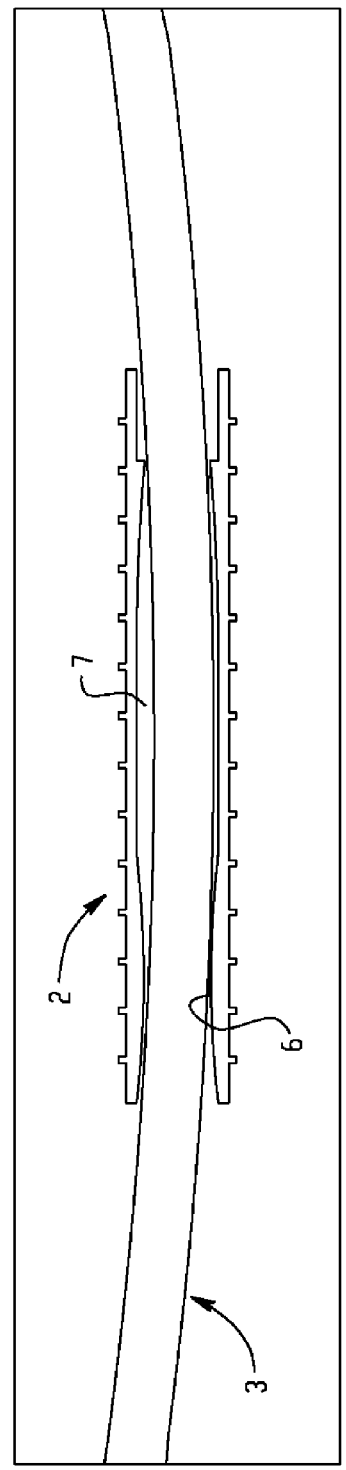

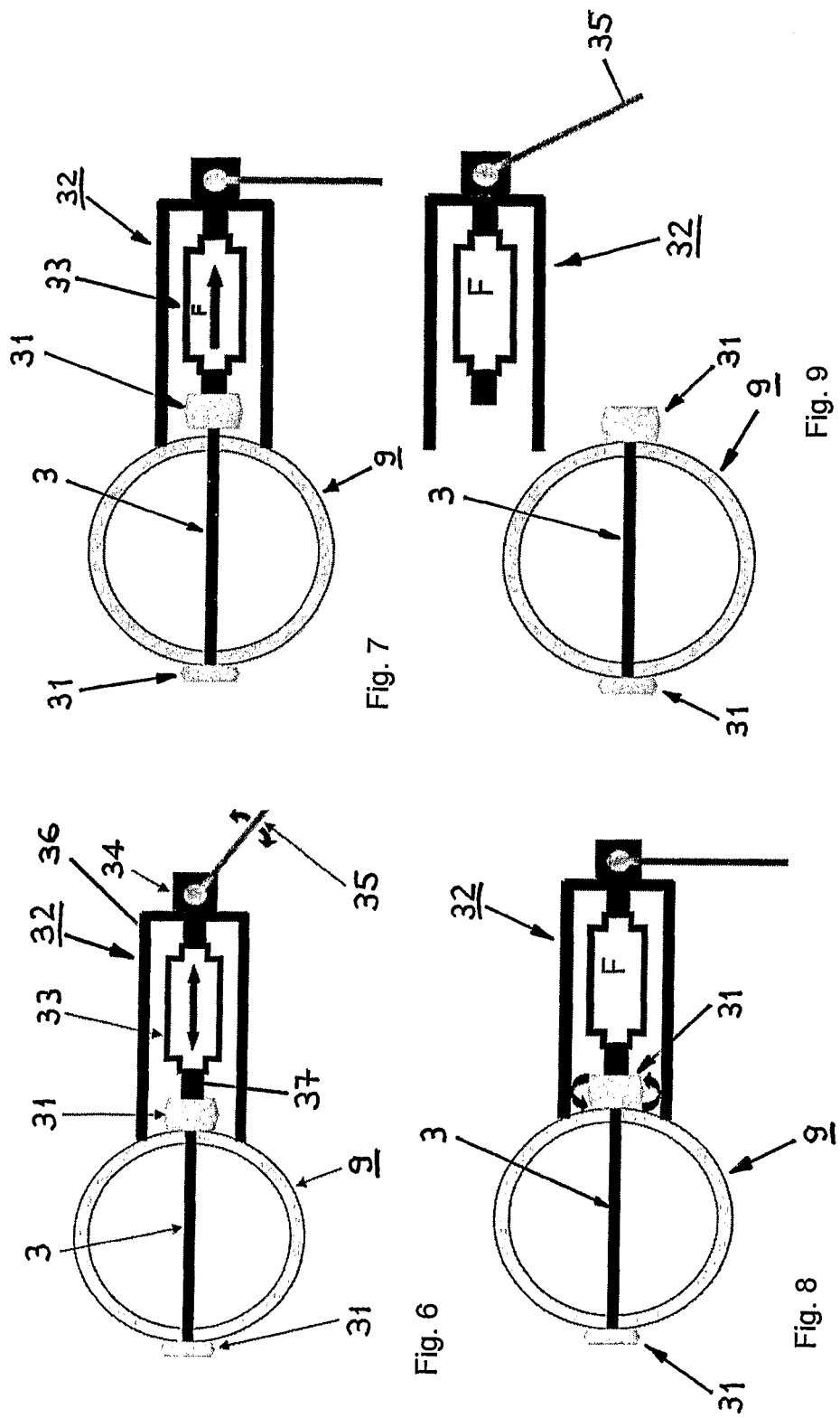

SLEEVE FOR A TRANSFIXATION DEVICE FOR AN EXTERNAL SKELETAL FIXATOR

FIELD OF THE INVENTION

The invention relates to a sleeve for a transfixation device for an external skeletal fixator, to a transfixation device for an external skeletal fixator comprising such a sleeve, to an external skeletal fixator comprising one or more transfixation devices and to a method for bone fracture healing

DESCRIPTION OF THE PRIOR ART

It is well known to fix long bone fractures with external fixation devices. The principle is that the load from one bone fragment to the other is transferred via combinations of pins, rings, bars and/or casts. The potential problem with these known devices is that the loading elements (e.g. pins) which are placed through the bone inevitably bend due to the transfer of load to an outer structure. Bending of the loading elements as they pass through the bone results in high local bone strains at the implant-bone interface. This leads to an undesired resorption of the bone and a loosening of the loading elements and thus to a premature failure of the fixation.

SUMMARY OF THE INVENTION

It is an object of the invention to provide a sleeve for a transfixation device for an external skeletal fixator which allows to avoid implant loosening at the bone/implant interface of the external fixation device. It is a further object of the invention to provide a transfixation device for an external skeletal fixator comprising such a sleeve and to provide an external skeletal fixator comprising one or more transfixation devices. An additional object of the invention is to provide a method for bone healing using such an external skeletal fixator.

The invention is based on a sleeve of a new sleeve and pin mechanism to transfer the load from the bone to the outer structure of the external skeletal fixator and vice versa. The transfixation device according to the invention comprises a sleeve which is inserted into the bone. Through this sleeve a pin is placed resting on supports within the sleeve. The load from the bone is applied through the sleeve to the pin which transfers the load to said outer structure. The pin/sleeve transfixation device is designed such that the pin may bend within the sleeve without the sleeve bending within the bone which reduces bending stresses and bone resorption at the bone-sleeve interface. The rate of loosening of the implants in the bone shall thus be reduced.

The advantages of the device according to the invention are the following:
a) stresses and strains at the bone-sleeve interface can be minimized when the bone is loaded;
b) upon applying load to the limb by the patient, the load is transferred from the proximal portion of the bone to the surface of the cylindrical sleeve. The force is then transferred to the pin of the external skeletal fixator by means of the pin-sleeve contact points (inner narrowings of the sleeve);
c) the pin-sleeve interaction is such that as the pin bends, the contact between the pin and sleeve is limited. Therefore, the pin bending does not exert bending reaction loads on the sleeve which reduces the strains at the bone-sleeve interface;
d) a significant decrease of the strains at the bone-sleeve interface results in annulling local bone resorption and consequent pin loosening.

In a preferred embodiment said at least two contractions are arranged symmetrically to the symmetry plane of said sleeve orthogonal to said longitudinal axis.

In another said at least two contractions are disposed at a distance A corresponding essentially to the distance between the two cortices of the long bone to be traversed by said sleeve.

In a further embodiment said distance A is minimum in a range between 10 mm and 35 mm.

In yet another embodiment said distance A is maximum in a range between 35 mm and 50 mm.

In still a further embodiment said sleeve and said at least two contractions are configured as a one-piece sleeve member.

In another embodiment said lumen is barrel-shaped between said at least two contractions. This allows the advantage that the preferably barrel-shape of the lumen between the contractions allows an enhanced bending of the pin. The contact areas between the pin and the sleeve are larger than line-shaped and not concentrated on a ring.

In still another embodiment said lumen comprises axially outside said contractions each an enlargement tapering preferably conically towards said contractions. This allows the advantage that the conical shape axially outside the contractions allows an enhanced bending of the pin. The contact areas between the pin and the sleeve are larger than line-shaped and not concentrated on a ring.

In a further embodiment said at least two contractions are configured in the form of separate supports connected to said interior wall of said sleeve. In particular embodiments the number of supports can vary between five and six.

In yet a further embodiment said contractions are configured as ring-shaped narrowings of said lumen coaxially arranged to said longitudinal axis. This allows the advantage that the geometry, particularly the diameters of the lumen and the first and second narrowing can be selected such that the pin is permitted to bend without touching the interior wall of the sleeve except on the narrowings which act as supports.

In another embodiment said contractions have a convex, preferably semicircularly convex shape towards said longitudinal axis in a longitudinal cross section of said sleeve. This allows the advantage that due to the convex shape of the supports a point contact between each narrowing and the peripheral surface of the inserted pin can be established.

In still another embodiment said sleeve is provided with an outer thread. This allows the advantage that the outer thread facilitates insertion of the sleeve into the bone.

In a further embodiment said sleeve has an overall length L, whereby a first of said at least two contractions is disposed at a distance D1 from a first end of said sleeve in the range of 5% to 20% of said overall length L and a second of said at least two contractions is disposed at a distance D2 from the first end of said sleeve in the range of 80% to 95% of said overall length L.

In a preferred embodiment of the transfixation device said pin(s) are provided with means at their free ends allowing a connection to said external supporting structure of an external skeletal fixator. This means can be configured as external threads allowing a fixation of the pin at the external supporting structure by a nut at each end.

In a preferred embodiment of the external skeletal fixator said external supporting structure comprises tensioning means for tensioning said pin(s) of said transfixation devices. This allows the advantage that the tensioning of said pins results in a decrease of pin bending in the sleeve and to a decrease of fragment displacement. It allows transferring higher loads to the external structure compared to the untensioned pin. This can be due to strain-hardening of the pin by stretching and/or due to the fact that since the pin has a small diameter it can be approximately regarded as a cable such only transferring tensile forces so that according to the support reaction and the combination and resolution of concurrent forces in statics a pretensioning of the pin results in a lower deflection.

The tensioning means may also be used to adjust the flexibility of the whole external skeletal fixator device which is influential for fracture healing.

The tensioning of the pins has the further advantage to ensure even loading where multiple pins are used in an external skeletal fixator. It further allows a controlled destabilization of a fracture to accelerate fracture healing.

In another embodiment said tensioning means are realised by:
a) an external thread at each end of the pin and a nut each with an internal thread matching said external thread and each of said nuts being axially kept by the external supporting structure; and
b) a tensioning device reversibly attachable to one end of the pin and allowing to exert a tensile force on the pin.

In a preferred embodiment said method further comprises the following steps applied for each pin to be inserted:
threadably mounting a nut at each end of said pin axially outside of said external supporting structure;
connecting a tensioning device terminally to one end of said pin;
exerting a tensile force on said pin by means of said tensioning device;
tightening of the nut previously mounted to that end of the pin where said tensioning device is attached; and
removing the tensioning device.

In another embodiment the step of exerting a tensile force further comprises the step of reading off the amount of the exerted tensile force on a scale or on a display. This allows the advantage that a defined prestress of the pin allows an optimum increase of the stiffness of the pin.

In a further embodiment said tensile force is minimum in the range between 5,500 N and 7,000 N.

In another embodiment said tensile force is maximum in the range between 7,500 N and 10,500 N.

The sleeve, the separate supports as well as the pin are made of a biocompatible metal, preferably stainless steel, e.g. the following combination:
Supports: MP35N, sleeve: 316L and pin MP35N.
Preferred dimensions the sleeve and pin are:
outer diameter of the sleeve: 8 mm
diameter of the lumen: 6 mm
length of the sleeve (e.g. for horses): 45 mm to 55 mm
diameter of the pin: 4 mm to 5 mm.

The pin is preferably configured circular cylindrical. Further, in order the have the diameters of the pin-sleeve mechanism be dimensioned approximately as a conventional pin the outer diameter of the sleeve is preferably equal or slightly bigger than the diameter of the conventional pins. The diameter of the pin according to the invention is less but the decreased mechanical properties of this pin compared to conventional pins are compensated by tensioning the pin.

A BRIEF DESCRIPTION OF THE DRAWINGS

Special embodiments of the invention are described in the following by way of example and with reference to the accompanying drawings in which:

FIG. 3 illustrates a longitudinal section of the pin-sleeve mechanism with another embodiment of the sleeve according to the invention in the unloaded state;

FIG. 4 illustrates a longitudinal section of the pin-sleeve mechanism of the embodiment of FIG. 3 under load;

FIG. 6 illustrates a top view onto the device of FIG. 5 including a tensioning means;

FIG. 7 illustrates a top view onto the device of FIGS. 5 and 6 during exertion of a tensile force;

FIG. 8 illustrates a top view onto the device of FIGS. 5 and 6 during tightening of the nut; and FIG. 9 illustrates a top view onto the device of FIGS. 5 and 6 with the tensioning means being demounted.

Figure 1:
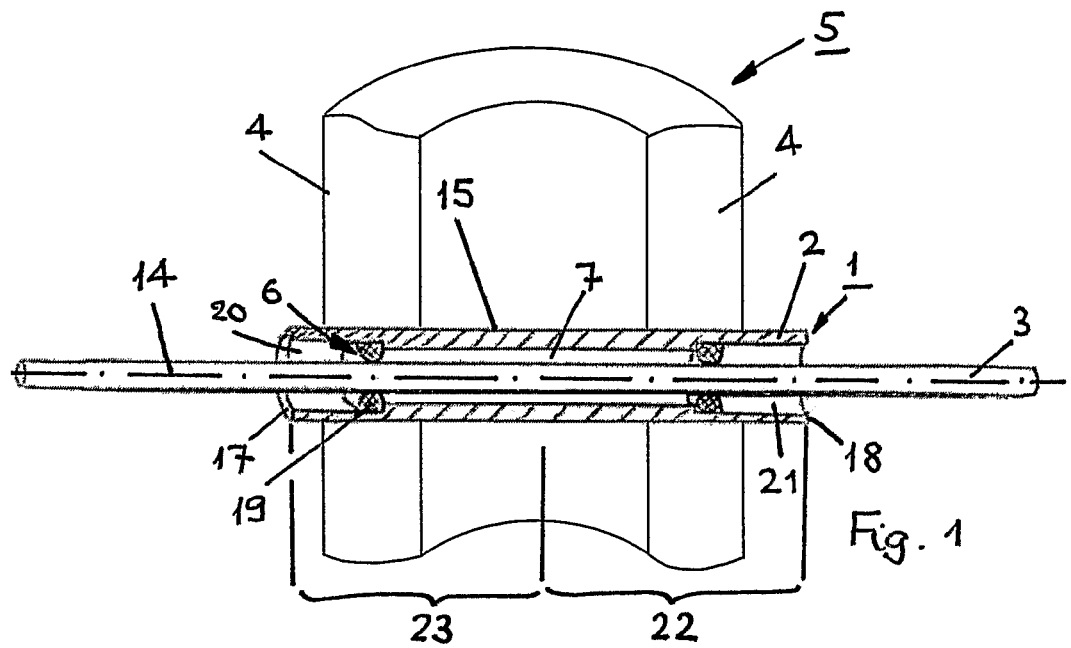
FIG. 1 illustrates a longitudinal section of the pin-sleeve mechanism comprising an embodiment of the sleeve according to the invention in the unloaded state.

FIG. 1 illustrates the pin-sleeve mechanism of a transfixation device 1 comprising an embodiment of the sleeve 2 according to the invention and a pin 3. The sleeve 2 comprises a longitudinal axis 14, a right portion 22, a left portion 23, an outer wall 16 and a lumen 7. The sleeve 2 can be made of biocompatible metal is implantable across the opposed cortices 4 of a long bone 5. Said lumen 7 is adapted for receiving said pin 3 which is connectable to an external supporting structure 9 (FIG. 5) of an external skeletal fixator 8. Further, said lumen 7 has two equal contractions 6, one each of said contractions 6 being located in said right respectively left portion 22;23 of said sleeve 2. Said contractions 6 serve as supports for the pin 3 inserted through the lumen 7 of the sleeve 2. In this embodiment said contractions 6 are configured as ring-shaped separate supports 19 concentric to the longitudinal axis 14. Towards the longitudinal axis 14 the contractions 6 are convexely, e.g. semicircularly shaped in a cross section parallel to the longitudinal axis 14 and define a minimum, inner diameter of the lumen 7. Said contractions 6 are symmetrically positioned at a mutual distance A and adequately far from the first and second end 17;18 of the sleeve 2. In order to mount said ring-shaped supports 19 at their correct position said lumen 7 is provided with a first and second enlarged portion 20;21 arranged towards the first respectively second end 17;18 of said sleeve 2. In the embodiment shown here, the supports 19 are separate members and one each can be pressed into the first respectively second enlarged portion 20;21 until it abuts at the shoulder formed between the central portion of the lumen 7 between said contractions 6 and the first respectively second enlarged portion 20;21. Due to the convex shape of the supports 19 in a cross section parallel to the longitudinal axis 14 a point contact between each narrowing and the peripheral surface of the inserted pin 3 is established. The solid pin 3 is made of a high tensile strength material and has a circular cylindrical shape with a diameter fitting the inner passage of the supports 19 in the lumen 7 of the sleeve 2.

Figure 2:
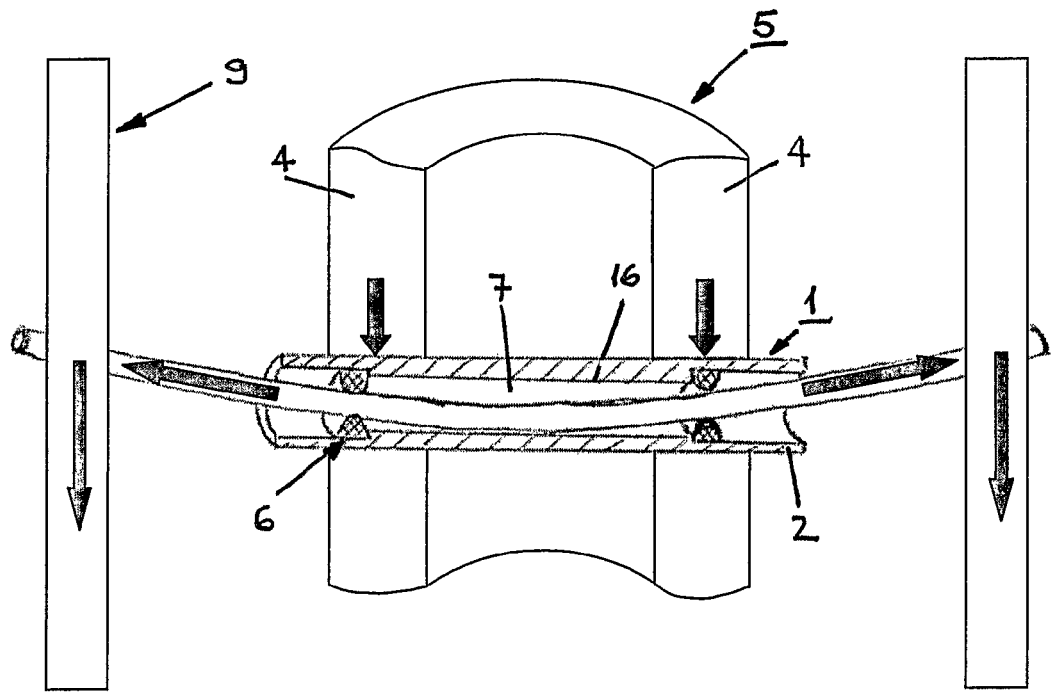
FIG. 2 illustrates a longitudinal section of the pin-sleeve mechanism of the embodiment of FIG. 1 under load.

FIG. 2 illustrates the pin-sleeve mechanism under load. The load transfer from that bone segment of the long bone 5 where the pin 3 is inserted to the outer supporting structure 9 of the external fixator 8 (FIG. 3) is subsequently effected from the bone 5 to the sleeve 2, from the sleeve 2 to the pin 3 and from the pin 3 to the external supporting structure 9 of the external skeletal fixator 8. The pin 3 is allowed to bend within the lumen 7 of said sleeve 2 in consequence of the applied load while the sleeve 2 itself does not bend due to the point wise load transfer from the sleeve 2 to the pin 3 in the respective bone sections. The load transfer from the bone 5 to the outer supporting structure 9 is indicated by arrows. The geometry, particularly the diameters of the central portion of said lumen 7 between said contractions 6 and the first and second enlarged portion 20;21 are selected such that the pin 3 is permitted to bend without touching the interior wall 16 of the sleeve 2 except on the supports 19.

The embodiment of the sleeve 2 illustrated in FIGS. 3 and 4 differs from the embodiment illustrated in FIGS. 1 and 2 only therein that the sleeve 2 and said contractions 6 are configured as a one-piece sleeve member and that said lumen 7 has an interior wall 16 having a convex, preferably barrel-like shape between said contractions 6 and axially outside said contractions 6 each an enlargement tapering conically towards said contractions 6. Further, said sleeve 2 has an outer thread 24 on an outer wall 15 to facilitate insertion into the bone 5. FIG. 3 illustrates the pin-sleeve mechanism in the unloaded state while FIG. 4 illustrates the same embodiment under load.

Figure 5:
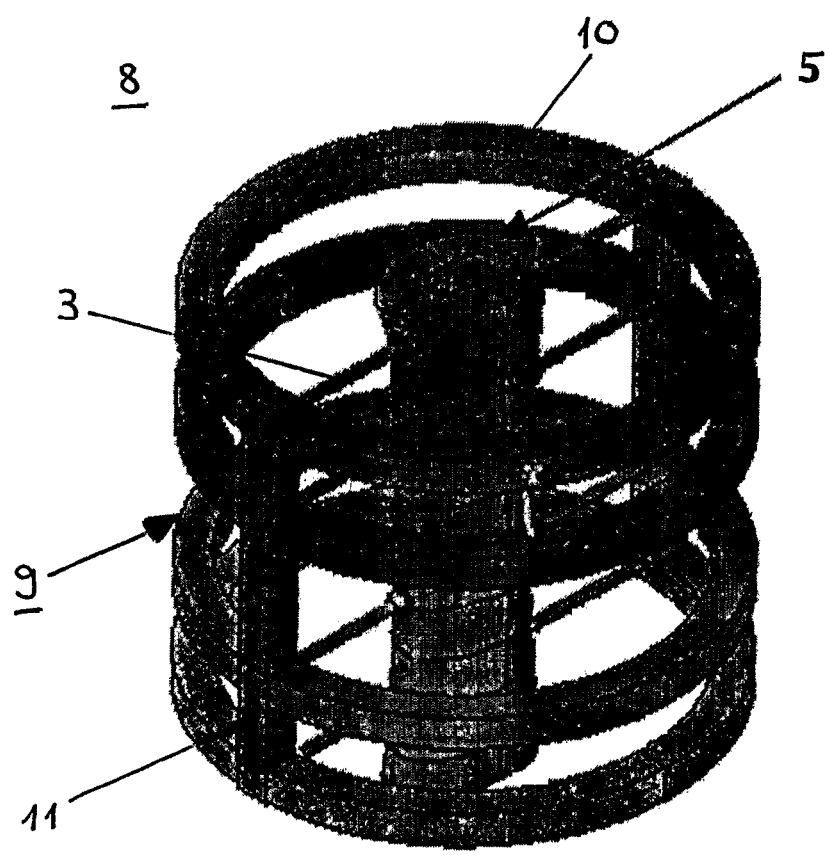
FIG. 5 illustrates a schematic perspective view of an embodiment of the device according to the invention including an outer supporting structure.

FIG. 5 exemplarily illustrates an external skeletal fixator 8 as known in the art. This external skeletal fixator 8 essentially comprises four ring collars 10 arranged coaxially to the central axis of the long bone 5 and at a certain distance to each other. The ring collars 10 are mutually connected by two posts 11 arranged diametrically with respect to the ring collar 10 such forming a rigid external supporting structure 9 of a external skeletal fixator 8. The ends of the four pins 3 passing the long bone 5 are each connected to one of the posts 5. Thereby, each of the four pins 3 are arranged at a location coinciding with the location of one of the ring collars 10.

An exemplary tensioning device 32 connected to the external supporting structure 9 is illustrated in FIG. 6. Said tensioning device 32 essentially comprises a housing 36 or frame, a tensioning member 37 arranged in said housing 36 or frame and being slideable coaxially to said pin 3, a force transducer 33, and an eccentric tensioning mechanism 34 located at the terminal end of said tensioning member 37 and being manually operatable by means of a lever 35. The front end of said housing 36 or frame laterally abuts the external supporting structure 9 such that an axial tensile force can be exerted onto said pin 3 by axially pulling said tensioning member 37 in a direction away from the external supporting structure 9. The tensile force onto the tensioning member 37 is exerted by means of said eccentric tensioning mechanism which is supported on said external supporting structure 9 via said housing 36. Said force transducer 33 allows reading off the amount of the exerted tensile force on a scale or display.

The method for bone fracture healing including tensioning the pin according to the invention is exemplarily illustrated in FIGS. 5 to 9. In this embodiment the method comprises the steps of:

a) drilling a plurality of transverse holes into a fractured long bone 5, whereby at least one hole is drilled in each bone fragment;
b) inserting a sleeve 2 in each of the drilled holes;
c) inserting a pin 3 through the lumen (not shown) of each inserted sleeve 2;
d) connecting each pin 3 to an external supporting structure 9 of an external skeletal fixator 8;
e) threadably mounting a nut 31 at each threaded end of said pin 3 axially outside of said external supporting structure 9;
f) connecting a tensioning device 32 to one threaded end of said pin 3 either terminally to one threaded end of said pin 3 or to an interior thread in one threaded end of said pin 3;
g) exerting a tensile force on said pin 3 by means of said tensioning device 32, whereby a lever 35 connected to an eccentric tensioning mechanism 34 of the tensioning device 32 is pulled on thereby introducing a tension on the pin 3. The applied tension can be read from a display or scale on a force transducer 33 located between the lever 35 and the pin 3;
h) tightening of the nut 31 previously mounted to that end of the pin 3 where said tensioning device 32 is attached; and
i) loosening the lever 35 and removing the tensioning device 32.

While various descriptions of the present invention are described above, it should be understood that the various features can be used singly or in any combination thereof. The scope of the present invention is accordingly defined as set forth in the appended claims.

What is claimed is:

1. A transfixation device for connection to an external supporting structure of an external skeletal fixator, said transfixation device comprising:
   a sleeve having a longitudinal axis, a first open end, a second open end, an outer wall, an interior wall and a lumen; and
   a pin having opposed ends each configured for connection to the external supporting structure of the external skeletal fixator;
   wherein the pin is configured to be received within the lumen of said sleeve, with the opposed ends of the pin connected to the external supporting structure of the external skeletal fixator, when said sleeve is implanted across opposed cortices of a bone,
   wherein said lumen comprises at least two longitudinally spaced apart contractions monolithically formed as part of the sleeve,
   wherein a first of said at least two contractions is located inward of the first open end in a first halving portion of the sleeve,
   wherein a second of said at least two contractions is located inward of the second open end in a second halving portion of the sleeve,
   wherein said at least two contractions have a form allowing them to serve as supports for said pin when the pin is received within said lumen thereby preventing contact between said pin and said interior wall except at said at least two contractions.

2. The transfixation device according to claim 1, wherein said at least two contractions are disposed a distance A from each other, said distance A being in a range between 10 mm and 50 mm.

3. The transfixation device according to claim 2, wherein said distance A is in a range between 10 mm and 35 mm.

4. The transfixation device according to claim 2, wherein said distance A is in a range between 35 mm and 50 mm.

5. The transfixation device according to claim 1, wherein said lumen comprises, axially outside each of said at least two contractions, an enlargement tapering towards said contractions.

6. The transfisation device according to claim 5, wherein the enlargement tapers conically toward said at least contractions.

7. The transfixation device according to claim 1, wherein said at least two contractions have a convex shape extending toward said longitudinal axis when viewed in a longitudinal cross section of said sleeve taken through said longitudinal axis.

8. The transfixation device according to claim 7, wherein said at least two contractions have a semicircularly convex shape extending toward the longitudinal axis in the longitudinal cross section of said sleeve taken through said longitudinal axis.

9. The transfixation device according to claim 1, wherein said at least two contractions are arranged symmetrically to a symmetry plane of said sleeve orthogonal to said longitudinal axis.

10. The transfixation device according to claim 1, wherein said lumen is barrel-shaped between said at least two contractions.

11. The transfixation device according to claim 1, wherein said contractions are ring-shaped narrowings of said lumen coaxially arranged with respect to said longitudinal axis.

12. The transfixation device according to claim 1, wherein said sleeve is provided with an outer thread.

13. The transfixation device according to claim 1, wherein said sleeve has an overall length L, wherein a first of said at least two contractions is disposed a distance D1 from the first open end of said sleeve, said distance D1 being in a range of 5% to 20% of said overall length L, and wherein a second of said at least two contractions is disposed a distance D2 from the first open end of said sleeve, said distance D2 being in a range of 80% to 95% of said overall length L.

14. An external skeletal fixator comprising:
a transfixation device according to claim 1; and
an external supporting structure to which opposed ends of the pin of said transfixation device are connectable to when said sleeve of said transfixation device is implanted across opposed cortices of a bone and the pin is received within the lumen of said sleeve.

15. The external skeletal fixator according to claim 14, wherein said external supporting structure further comprises tensioning means for exerting a tensile force on said pin of said transfixation device.

16. The external skeletal fixator according to claim 15, wherein external threads are formed at each opposed end of the pin, and wherein said tensioning means comprises:
a) a pair of nuts, each nut being provided with an internal thread that matches at least one of said external threads formed at each opposed end of the pin, wherein each of said nuts is threaded onto one end of the pin and axially maintained against the external supporting structure; and
b) a tensioning device reversibly attachable to one end of the pin that is configured to exert a tensile force on the pin.

17. A method for bone fracture healing comprising:
A) drilling a plurality of transverse holes into a fractured bone, whereby at least one hole is drilled in a bone fragment;
B) inserting a sleeve of a transfixation device according to claim 1 in each of the drilled holes;
C) inserting the pin of the transfixation device through each lumen of each inserted sleeve; and
D) connecting the opposed ends of the pin to an external supporting structure of an external skeletal fixator.

18. The method according to claim 17, further comprising:
E) threadably mounting a nut at each end of said pin axially outside of said external supporting structure;
F) connecting a tensioning device terminally to one end of said pin;
G) exerting a tensile force on said pin by means of said tensioning device;
H) tightening the nut previously mounted to the end of the pin where said tensioning device is connected; and
I) removing the tensioning device.

19. The method according to claim 18, further comprising reading the amount of the exerted tensile force exerted in step G) on a scale or on a display.

20. The method according to claim 18, wherein said tensile force is in a range between 5,500 N and 7,000 N.

21. The method according to claim 18, wherein said tensile force is in a range between 7,500 N and 10,500 N.

* * * * *